(12) United States Patent
Delaney et al.

(10) Patent No.: US 11,638,646 B1
(45) Date of Patent: May 2, 2023

(54) BIOCERAMIC IMPLANTS MATCHED TO PATIENT SPECIFIC AND BONE SPECIFIC GEOMETRY

(71) Applicant: 3D Biomaterials, Santa Cruz, CA (US)

(72) Inventors: David Christopher Delaney, Scotts Valley, CA (US); Duran N Yetkinler, San Jose, CA (US)

(73) Assignee: 3D Biomaterials, Inc., Santa Cruz, CA (US)

( * ) Notice: Subject to any disclaimer, the term of this patent is extended or adjusted under 35 U.S.C. 154(b) by 351 days.

(21) Appl. No.: 16/995,666

(22) Filed: Aug. 17, 2020

Related U.S. Application Data

(60) Provisional application No. 62/888,186, filed on Aug. 16, 2019.

(51) Int. Cl.
| | |
|---|---|
| *A61F 2/30* | (2006.01) |
| *B33Y 10/00* | (2015.01) |
| *A61F 2/28* | (2006.01) |
| *B28B 1/00* | (2006.01) |
| *B33Y 50/00* | (2015.01) |
| *B33Y 80/00* | (2015.01) |
| *B33Y 70/00* | (2020.01) |

(52) U.S. Cl.
CPC ........ *A61F 2/30942* (2013.01); *A61F 2/2875* (2013.01); *B28B 1/001* (2013.01); *B33Y 10/00* (2014.12); *B33Y 50/00* (2014.12); *B33Y 70/00* (2014.12); *B33Y 80/00* (2014.12); *A61F 2002/30948* (2013.01); *A61F 2002/30957* (2013.01); *A61F 2002/30985* (2013.01); *A61F 2310/00179* (2013.01); *A61F 2310/00221* (2013.01); *A61F 2310/00293* (2013.01)

(58) Field of Classification Search
CPC ........ A61F 2/30942; A61F 2002/30948; A61F 2/2875
See application file for complete search history.

(56) References Cited

U.S. PATENT DOCUMENTS

| | | | |
|---|---|---|---|
| 9,020,788 B2 * | 4/2015 | Lang .................. | A61B 17/1764 703/6 |
| 2009/0068245 A1 * | 3/2009 | Noble .................... | A61L 27/56 521/142 |

(Continued)

OTHER PUBLICATIONS

Staffa et al. Custom made cranioplasty prostheses in porous hydroxyapatite using 3D design techniques: 7 years experience in 25 patients. Acta Neurochir (Wien) (2007) 149: 161-170 (Year: 2007).*

*Primary Examiner* — Cachet I Proctor
(74) *Attorney, Agent, or Firm* — Rimon Law, P.C.

(57) ABSTRACT

The production of bioceramic powders and bioceramic implants are described and an additive manufactured implant used for tissue reconstruction and a method for manufacturing the implant are disclosed. The implant may be fabricated at least in part from suitable bioceramic powders produced using tailored mineral compositions tailored to the unique material properties of the tissue being replaced. The implants may be tailored to a three-dimensional shape and mechanical properties of the tissue defect designed to be replaced by surgical implantation of the device. Native tissue repair and regeneration at the site of implantation are also provided.

16 Claims, 6 Drawing Sheets

(56) References Cited

U.S. PATENT DOCUMENTS

| | | | |
|---|---|---|---|
| 2010/0145469 A1* | 6/2010 | Barralet | B33Y 10/00 |
| | | | 427/2.24 |
| 2010/0292146 A1* | 11/2010 | Seibl | A61F 2/28 |
| | | | 514/8.8 |
| 2011/0040389 A1* | 2/2011 | Da Silva Santos | A61L 27/425 |
| | | | 623/23.61 |
| 2016/0235536 A1* | 8/2016 | Barthelat | A61L 27/222 |
| 2017/0014169 A1* | 1/2017 | Dean | A61B 17/8071 |
| 2018/0110593 A1* | 4/2018 | Khalil | A61C 8/0095 |
| 2019/0231531 A1* | 8/2019 | Gordon | A61F 2/2875 |

* cited by examiner

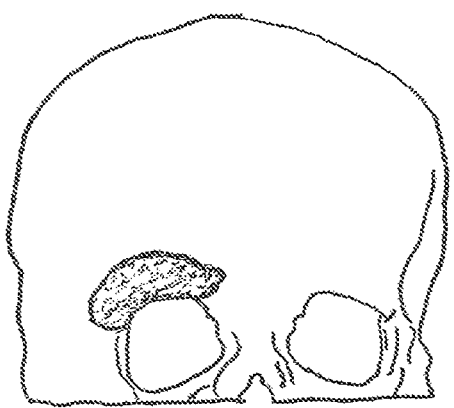
FIG. 1A
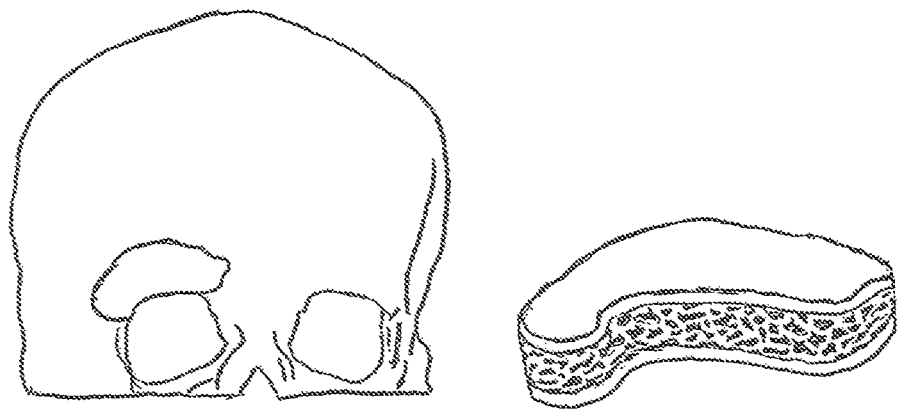
FIG. 1B
FIG. 1C

| Sample | Length (mm) | Width (mm) | Height (mm) | Color | Load at Failure (N) | Flexural Strength (MPa) |
|---|---|---|---|---|---|---|
| 1 | 37.3 | 2.5 | 3.07 | white | 42 | 96 |
| 2 | 36.0 | 2.4 | 2.95 | grey | 48 | 123 |
| 3 | 36.0 | 2.4 | 2.97 | grey | 46 | 116 |
| 4 | 35.9 | 2.4 | 2.97 | grey | 48 | 122 |
| 5 | 36.0 | 2.4 | 2.97 | grey | 48 | 123 |
| 6 | 35.9 | 2.4 | 2.97 | grey | 49 | 125 |
| 7 | 36.1 | 2.4 | 3.01 | grey | 54 | 136 |
| | | | | | | Average = 118 MPa |

Fig. 2

BIOCERAMIC IMPLANTS MATCHED TO PATIENT SPECIFIC AND BONE SPECIFIC GEOMETRY

CROSS-REFERENCE TO RELATED APPLICATIONS

This application claims the benefit of U.S. Provisional Application No. 62/888,186 filed on Aug. 16, 2019, and entitled "Production of Bioceramic Powders Suitable For 3D Printing And Powder Injection Molded Bioceramic Implants" which is incorporated herein by reference.

BACKGROUND

Field of the Invention

This invention relates in general to the field of orthopedic implants. More specifically the invention relates to a medical implant for repair of a bone defect. Uses include craniofacial implant design and production, reconstructive surgery implants, orthopedic and spinal implants, bone tendon suture anchors, and spinal implants.

Related Art

Implant materials used to replace bone can be categorized into autograft, allograft, and synthetic, man-made materials. Manufactured materials that do not have biological activity (bio-inert) include materials such as polyethylene, metals such as titanium and stainless steels, wear resistant ceramics such as Zirconia/Alumina and Silicon Nitride. So called bioactive or bone friendly ceramic materials (bioceramic) have recently seen technological advancements so that materials such as hydroxyapatite and similar calcium phosphates can now be manufactured using additive manufacturing techniques such as 3D printing and ceramic injection molding. Computer-aided design based on medical imaging and 3D printing have resulted in patient-specific, custom fit implants made from both bio-inert and bioactive materials. There are current methods to manufacture implants that mimic the patients' anatomy and match the design of the implant to geometrically fit individual gross anatomy.

Studies have demonstrated that bioceramics that closely match the microarchitecture of bone and implant materials that closely match the mechanical properties of bone, when implanted, result in a reduction of implant associated complications and improved bone healing. There exists a need for implants that mimic native bone material properties such as porosity, mechanical strength, density, and bioactivity. Of particular interest is the surgical repair of cranial defects with patient matched implants. Cranioplasty, the surgical repair of a defect or deformity of the skull, is a significant aspect of surgery targeting cranial vault tumors, infection, trauma, or congenital defects. Also of interest is the surgical repair of spinal defects with patient matched implants. Such implants include vertebral spacers or cages. Spinal fusion or vertebral fracture repair is often accomplished using implants that would benefit from improved implant properties.

SUMMARY OF THE INVENTION

The current invention describes bioceramic implants matched to the bone architecture, bone microstructure at both the macro (mm scale) and micro (micron) scale while modeling an matching the bone mechanical properties of the individual patients' bone defect.

Embodiments include; a bioceramic implant, a method of making the bioceramic powder precursors, a method of making the finished bioceramic implant, and a method of arriving at the design for such bioceramic implant.

A method for the design and manufacturing the implant from bioceramic powders is described. The invention describes methods for synthesizing powders that are within a predetermined specification of elemental concentrations, surface area, microstructure, particle size, phase purity, and function. These activities include but are not limited to wet chemical formulation and synthesis, reaction, parameter optimization, full material characterizations including X-ray diffraction, scanning electron microscopy, and BET surface area analysis.

BRIEF DESCRIPTION OF THE DRAWINGS

FIG. 1A is a front view of a skull trauma defect.

FIG. 1B is a front view of an exemplary embodiment of a patient-specific cranial implant of the present invention designed to fill a bone void in a skull of a patient and to simultaneously match the mechanical and architectural microstructure of the missing bone.

FIG. 1C is a cross section through the cranial implant of FIG. 1B.

FIG. 2 is a table of bending strength of a test implant, according to various embodiments of the present invention.

DETAILED DESCRIPTION

Figure 3:
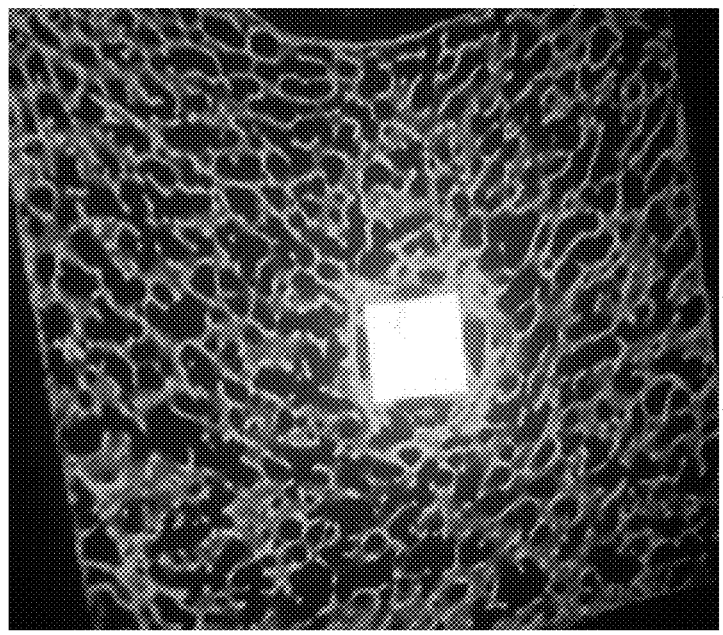
FIG. 3 is an in vivo X-ray of a test article implanted into mammalian long bone, according to various embodiments of the present invention.
Figure 4:
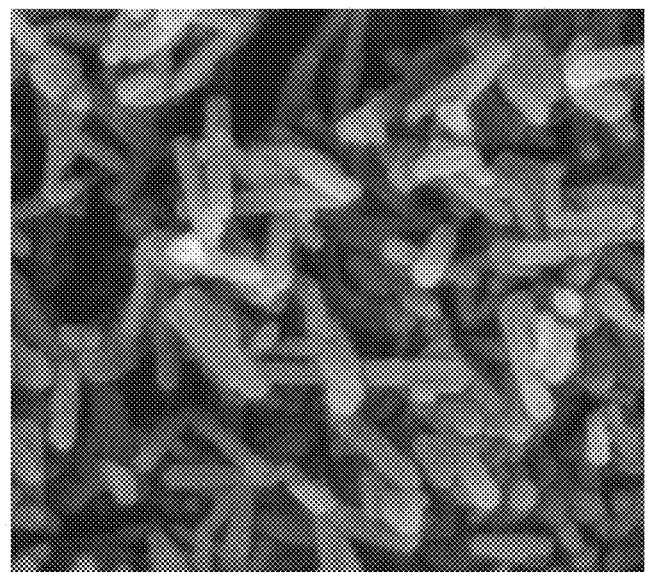
FIG. 4 is scanning electron micrograph of ceramic powder, according to various embodiments of the present invention.
Figure 5:
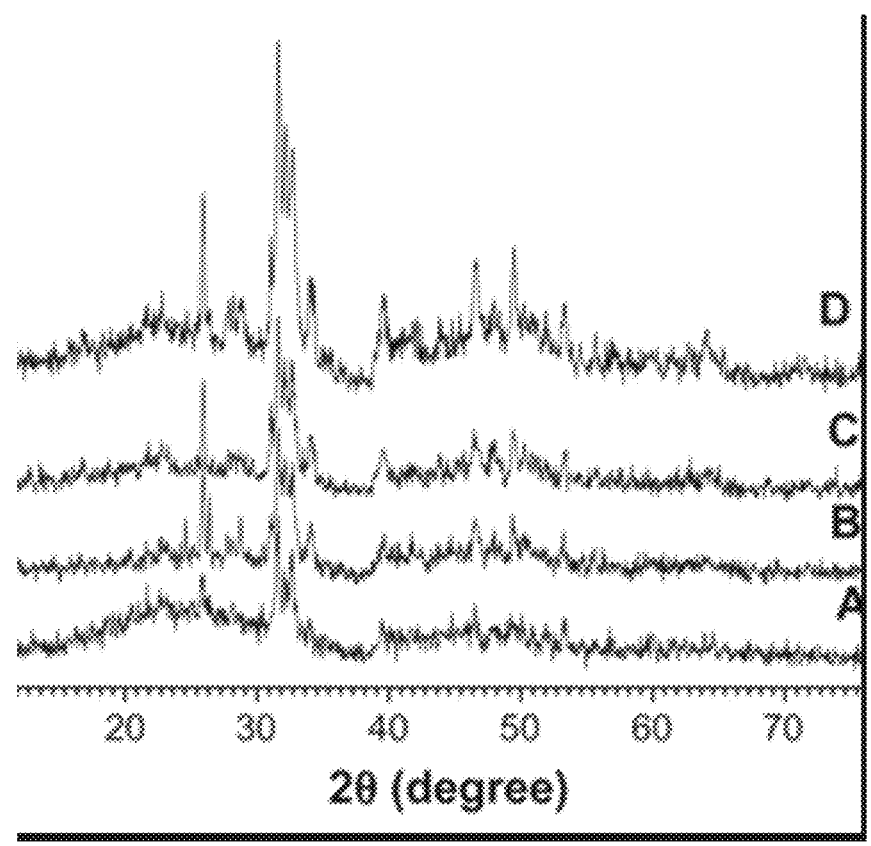
FIG. 5 is a powder X-ray diffractogram of ceramic powder, according to various embodiments of the present invention.

The invention describes production methods for producing bioceramic powders with tailored mineral compositions suitable for additive manufacturing such as 3D printing and ceramic injection molding to produce implants suitable for replacement and or repair of bone. Design of Cranial Implant as in FIG. 1B.

The design of a cranial implant can be accomplished according to Mitsouras et al, 2015, which provides a non-limiting example of a method for image acquisition, image processing and 3D print file generation (Mitsouras et al, 2015). The authors give examples of cranial implants made from 3D printed titanium (Mitsouras et al, 2015) and recreation and design for implants designed for complex fracture reconstruction (Mitsouras et al, 2015) that are matched to the patient's gross anatomical features. The method described by Mitsouras includes the acquisition of patient medical imaging data taken by computed tomography (CT), followed by data manipulation of the .DICOM file format, data processing of the image to ensure anatomical accuracy, file conversion to the .STL format, followed by further data processing such as smoothing and mirroring of anatomy to produce a 3D printable file of an implantable medical device. There are numerous, off the shelf CT segmentation software applications available to accomplish these image acquisition, slicing and analysis based anatomical reconstructions.

An embodiment of the current invention utilizes off the shelf image acquisition methodologies as referenced above as the starting point for further analysis by finite element, mechanical, microstructural, and anatomical data. These data are input in any one of several commercially available parametric modeling applications such as SolidWorks and used for the design of the implant that will closely match the bone segment being replaced. The implant as in 100 will have optimized porosity, mechanical strength, modulus of elasticity, and density among other designed parameters based on analyzed input imaging data.

An additional embodiment includes the optimization of ceramic precursor powders for production of the implant. Data from finite element modeling of bone CT images is accomplished by available software applications such as BoneMat, referenced here as one example, and used to arrive at the Young's modulus or modulus of elasticity. By selection and use of ceramic powders produced in an additional embodiment, the mechanical properties may be adjusted to that of the bone defect. Powders produced as described in this embodiment are used as feed stock in any number of additive manufacturing methods such as but not limited to stereolithography resin printing, multi-jet fusion, fused deposition modeling of ceramic powder/plastic filaments, and powder bed printing of ceramic powders. Examples of ceramic powder production are detailed below that are adjusted to meet different mechanical requirements when manufacturing an implant of desired strength, porosity, or modulus.

An additional embodiment utilizes the design and ceramic powders to produce by 3D printing in an SLA type resin printer with the optimized ceramic powders as dispersed at a weight percentage of approximately 50% by weight in photocured resin base that is commonly used in 3D printers such as those commercially available by Tethon 3D and others. The resin with intimately mixed ceramic powder is loaded into the resin tray and the implant printed from a .STL file. The resulting print is then partially debound in a graded series of isopropyl alcohol from 50% v/v, incrementally to 100% isopropyl alcohol in 10% v/v increments. Once partially debound the green part is placed in a vacuum or atmospherically controlled furnace where remaining resin is removed by controlled heating to approximately 400 C, followed by slow cooling to room temperatures. Once debound the "green" part is fired in a controlled atmosphere sintering furnace with a 1 degree C. per minute ramp rate and held at the sintering temperature of the ceramic, for calcium phosphate based powders this temperature can be from 1000 C to 1500 C. The temperature of the sintering program is held until densification of the part is accomplished followed by slow cooling at <2 C/minute to room temperature.

Figure 6:
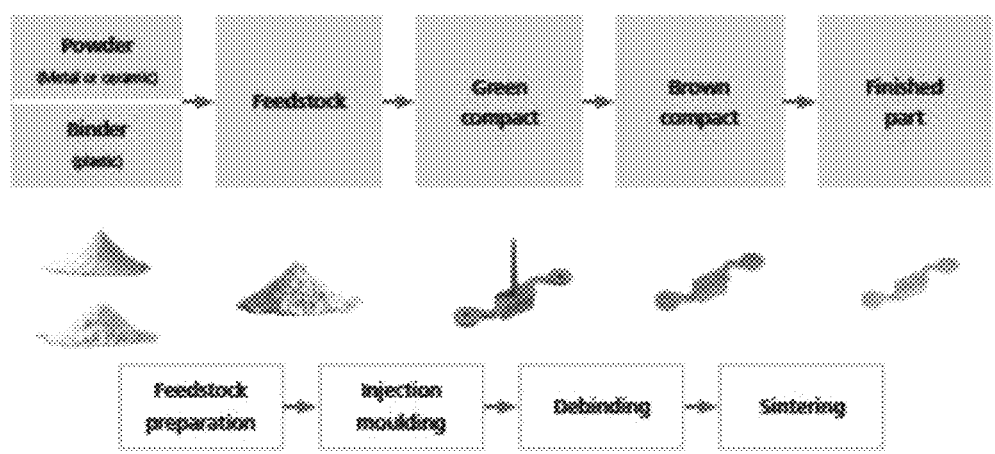
FIG. 6 is a schematic representation of a method according to a various embodiments of the present invention.

An additional embodiment utilizes ceramic injection molding to produce the implant. Ceramic powders of the subject invention are injection molded using a water soluble binder or combination of water soluble and water insoluble binders as in Mutsuddy and Ford. The process involves high sheer intimate mixing of ceramic precursor powders with a combination of binders, followed by molding, debinding and sintering, according to the FIG. 6.

The embodiment as described made by powder ceramic injection molding may be advantageous for a number of medical and non-medical applications.

EXAMPLE

Wet Chemical Formulation and Synthesis of Ceramic Powders used as feedstock for 3D printing and ceramic injection molding:

Synthesis of nano and sub-nano sized ceramic powders by a modified sol-gel technique or precipitation is utilized to obtain starting materials for additive manufacturing. These syntheses are optimized to incorporate varying amounts of atomic trace and major elements to produce powders of controlled crystal size, atomic element substitution and sintering parameters to produce powders of specific surface area and the resultant mechanical properties of solid bodies produced from the above powder(s). Materials are characterized utilizing ICP elemental analyses, powder X-ray diffraction, SEM, and BET surface area. These studies are essential to obtain tolerances for raw material selection used in additive manufacturing of bone replacement medical device implants.

Example 1. Sol-Gel Synthesis of Zinc Substituted Hydroxyapatite

Methods:
Solution A:
Ammonium phosphate (($NH_4$)$_2$HPO$_4$) and zinc nitrate hydrate (Zn(NO$_3$)$_2$.XH$_2$O) are dissolved in anhydrous ethanol with vigorous stirring.
Solution B:
Calcium nitrate hydrated salt (Ca(NO$_3$)$_2$.xH$_2$O) dissolved in anhydrous ethanol with vigorous stirring.
Precipitation Conditions:
Both solutions were heated to 95° C. under reflux. Solution A was rapidly added to Solution B. A pH stat pump (Etatron HD-pH, Rome, Italy) was utilized to maintain the resultant solution at pH=10.5. Temperature was maintained at 98° C. for 12 hours until an opaque gel formed. The resulting gel was washed with a descending ethanol series from 100%-0% in type 1 reagent grade distilled water, then dried under argon gas at 50° C. for 24 hours. The resultant submicron sized powder was analyzed by X-ray diffraction, scanning electron microscopy and ICP elemental analysis.

Optimization of solid body mechanical properties based on ceramic powder specifications:

Example 1, above describes production of a zinc substituted hydroxyapatite by sol-gel precipitation. When utilized in an SLA type 3-D printer (Form 2, Formlabs, Somerville Mass.), solid body constructs with specific mechanical properties of modulus and tensile strength can be printed. By varying the concentration of zinc nitrate in example 1 and thus the molar substitution of zinc in the apatite crystal lattice, the modulus and tensile strengths are optimized to specifications needed for a particular implant. Cationic substitutions are made by addition of the appropriate salts in place or in addition to zinc nitrate in solution A above. Examples include: Magnesium chloride, Manganese chloride, Iron oxide(s) and the like. Anionic substitutions also result in different mechanical properties for solid bodies printed using the same ceramic powder processing. Silicon as SiO$_4$ is substituted for PO$_4$ in the same manner by the addition of sodium silicate in partial addition to ammonium phosphate in Solution A above.

Example 2. Sol-Gel Synthesis of Magnesium Substituted Hydroxyapatite

Methods:
Solution A:

Ammonium phosphate (($NH_4$)$_2HPO_4$) and magnesium chloride hydrate ($MgCl_2.XH_2O$) are dissolved in anhydrous ethanol with vigorous stirring.

Solution B:

Calcium nitrate hydrated salt ($Ca(NO_3)_2.xH_2O$ dissolved in anhydrous ethanol with vigorous stirring.

Precipitation Conditions:

Both solutions were heated to 95° C. under reflux. Solution A was rapidly added to Solution B. A pH stat pump (Etatron HD-pH, Rome, Italy) was utilized to maintain the resultant
solution at pH=10.5. Temperature was maintained at 98° C. for 12 hours until an opaque gel formed. The resulting gel was washed with a descending ethanol series from 100%-0% in type 1 reagent grade distilled water, then dried under argon gas at 50° C. for 24 hours. The resultant submicron sized powder was analyzed by X-ray diffraction, scanning electron microscopy and ICP elemental analysis.

Optimization of solid body mechanical properties based on ceramic powder specifications:

Example 2, above describes production of a magnesium substituted hydroxyapatite by solgel precipitation. When utilized in an SLA type 3-D printer (Form 2, Formlabs, Somerville Mass.), solid body constructs with specific mechanical properties of modulus and tensile strength can be printed. By varying the concentration of magnesium chloride in example 1 and thus the molar substitution of magnesium in the apatite crystal lattice, the modulus and tensile strengths are optimized to specifications needed for a particular implant.

Example 3. Sol-Gel Synthesis of Manganese Substituted Hydroxyapatite

Methods:

Solution A:

Ammonium phosphate ($NH_4)2HPO_4$) and Iron III oxide ($MnCl_2.XH_2O$) are dissolved in anhydrous ethanol with vigorous stirring.

Solution B:

Calcium nitrate hydrated salt ($Ca(NO_3)_2.xH_2O$) dissolved in anhydrous ethanol with vigorous stirring.

Precipitation Conditions:

Both solutions were heated to 95° C. under reflux. Solution A was rapidly added to Solution B. A pH stat pump (Etatron HD-pH, Rome, Italy) was utilized to maintain the resultant solution at pH=10.5. Temperature was maintained at 98° C. for 12 hours until an opaque gel formed. The resulting gel was washed with a descending ethanol series from 100%-0% in type 1 reagent grade distilled water, then dried under argon gas at 50° C. for 24 hours. The resultant submicron sized powder was analyzed by X-ray diffraction, scanning electron microscopy and ICP elemental analysis.

Optimization of solid body mechanical properties based on ceramic powder specifications:

Example 1, above describes production of a manganese substituted hydroxyapatite by solgel precipitation. When utilized in an SLA type 3-D printer (Form 2, Formlabs, Somerville Mass.), solid body constructs with specific mechanical properties of modulus and tensile strength can be printed. By varying the concentration of manganese chloride in example 3 and thus the molar substitution of manganese in the apatite crystal lattice, the modulus and tensile strengths are optimized to specifications needed for a particular implant.

Example 4. Sol-Gel Synthesis of Iron Substituted Hydroxyapatite

Methods:

Solution A:

Ammonium phosphate ($NH_4)2HPO_4$) and Iron III Oxide ($Fe_2O_3$) are dissolved in anhydrous ethanol with vigorous stirring.

Solution B:

Calcium nitrate hydrated salt ($Ca(NO_3)_2.xH_2O$) dissolved in anhydrous ethanol with vigorous stirring.

Precipitation Conditions:

Both solutions were heated to 95° C. under reflux. Solution A was rapidly added to Solution B. A pH stat pump (Etatron HD-pH, Rome, Italy) was utilized to maintain the resultant solution at pH=10.5. Temperature was maintained at 98° C. for 12 hours until an opaque gel formed. The resulting gel was washed with a descending ethanol series from 100%-0% in type 1 reagent grade distilled water, then dried under argon gas at 50° C. for 24 hours. The resultant submicron sized powder was analyzed by X-ray diffraction, scanning electron microscopy and ICP elemental analysis.

Optimization of solid body mechanical properties based on ceramic powder specifications:

Example 4, above describes production of a iron substituted hydroxyapatite by sol-gel precipitation. When utilized in an SLA type 3-D printer (Form 2, Formlabs, Somerville Mass.), solid body constructs with specific mechanical properties of modulus and tensile strength can be printed. By varying the concentration of iron oxide in example 4 and thus the molar substitution of iron in the apatite crystal lattice, the modulus and tensile strengths are optimized to specifications needed for a particular implant.

Example 5. Sol-Gel Synthesis of Silicon Substituted Hydroxyapatite

Methods:

Solution A:

Ammonium phosphate (($NH_4)2HPO_4$) and zinc nitrate hydrate ($Zn(NO_3)2.XH_2O$) are dissolved in anhydrous ethanol with vigorous stirring.

Solution B:

Calcium nitrate hydrated salt ($Ca(NO_3)_2.xH_2O$, sodium silicate ($Na_2SiO_4$), and potassium silicate ($K_2SiO_3$) are dissolved in anhydrous ethanol with vigorous stirring.

Precipitation Conditions:

Both solutions were heated to 95° C. under reflux. Solution A was rapidly added to Solution B. A pH stat pump (Etatron HD-pH, Rome, Italy) was utilized to maintain the resultant solution at pH=10.5. Temperature was maintained at 98° C. for 12 hours until an opaque gel formed. The resulting gel was washed with a descending ethanol series from 100%-0% in type 1 reagent grade distilled water, then dried under argon gas at 50° C. for 24 hours. The resultant submicron sized powder was analyzed by X-ray diffraction, scanning electron microscopy and ICP elemental analysis.

Optimization of solid body mechanical properties based on ceramic powder specifications:

Example 5, above describes production of a silicon and/or silicate substituted hydroxyapatite by sol-gel precipitation. When utilized in an SLA type 3-D printer (Form 2, Formlabs, Somerville Mass.), solid body constructs with specific mechanical properties of modulus and tensile strength can be printed. By varying the concentration of potassium and sodium silicates in example 1 and thus the molar substitution of silicon in the apatite crystal lattice, the modulus and tensile strengths are optimized to specifications needed for a particular implant.

Examples 1-5 above may be combined in total, or in part to optimize powder elemental compositions while maintaining desired biocompatibility specifications for bioceramic powders utilized in additive manufacturing and production a variety of orthopedic and craniofacial implants.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

What is claimed is:

1. An additive manufacturing method for producing a bioceramic implant, the method comprising:
optimization of the implant's mechanical and physical properties to the mechanical and physical properties of the bone tissue being surgically repaired by examination of a patient's bone properties following X-ray/CT imaging, mechanical property prediction with computer modeling and manipulation of ceramic powder precursors used in the additive manufacturing process to produce the implant such that the implant is composed of primarily calcium phosphate, tailoring the ceramic precursor properties and thus ensuring implant material and mechanical properties closely match properties of bone tissue being replaced by said implant, where the resulting implant is used in a bone defect.

2. The method of claim 1 wherein the implant is shaped to match, in 3D space, the geometrical shape of the bone tissue prior to the injury suffered by the patient.

3. The method of claim 1 wherein the implant is shaped to match with sub-millimeter accuracy, the bone tissue architecture of preexisting bone prior to the injury suffered by the patient.

4. The method of claim 1 wherein the implant is shaped to match, in 3D space, the geometrical shape of a skull prior to the injury suffered by the patient.

5. The method of claim 1 wherein the calcium phosphate is a phase pure calcium phosphate.

6. The method of claim 1 wherein the calcium phosphate is a phase pure hydroxyapatite.

7. The method of claim 1 wherein the calcium phosphate is a transition metal substituted hydroxyapatite.

8. The method of claim 1 wherein the calcium phosphate is a metalloid substituted hydroxyapatite.

9. The method of claim 1 wherein the calcium phosphate is a phase pure whitlockite.

10. The method of claim 1 wherein the calcium phosphate is alpha-tricalcium phosphate.

11. The method of claim 1 wherein the calcium phosphate is beta tricalcium phosphate.

12. The method of claim 1 wherein the additive manufacturing process comprises ceramic 3D printing.

13. The method of claim 1 wherein the additive manufacturing process comprises ceramic injection molding.

14. The method of claim 1 wherein the implant is manufactured with specifications generated from finite element modeling of the mechanical properties of the site of bone implantation.

15. The method of claim 1 wherein the implant is manufactured with specifications generated from quantitative micro CT imaging of the microstructure of the site of bone implantation.

16. The method of claim 1 wherein the implant is manufactured with specifications generated from parametric modeling of the microstructure of the site of bone implantation.

* * * * *